US007851161B2

(12) United States Patent
Hoon et al.

(10) Patent No.: US 7,851,161 B2
(45) Date of Patent: Dec. 14, 2010

(54) EPIGENETIC SILENCING OF CYCLOOXYGENASE-2 AFFECTS CLINICAL OUTCOME IN GASTRIC CANCER

(75) Inventors: Dave S. B. Hoon, Los Angeles, CA (US); Michiel de Maat, Rotterdam (NL)

(73) Assignee: John Wayne Cancer Institute, Santa Monica, CA (US)

( * ) Notice: Subject to any disclaimer, the term of this patent is extended or adjusted under 35 U.S.C. 154(b) by 0 days.

(21) Appl. No.: 12/139,415

(22) Filed: Jun. 13, 2008

(65) Prior Publication Data

US 2009/0061441 A1  Mar. 5, 2009

Related U.S. Application Data

(60) Provisional application No. 60/943,812, filed on Jun. 13, 2007.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/23.5; 536/24.1

(58) Field of Classification Search .................. None
See application file for complete search history.

(56) References Cited

U.S. PATENT DOCUMENTS

| 2004/0170977 | A1 | 9/2004 | Laird | |
|---|---|---|---|---|
| 2006/0051768 | A1* | 3/2006 | Hoon et al. | 435/6 |
| 2007/0161029 | A1 | 7/2007 | Li et al. | |

OTHER PUBLICATIONS de Maat et al. Journal of Clinical Oncology. 2007. 25: 4887-4894.*
Bastian et al. European Urology. Mar. 2007. 51: 665-674.*
Nishiyama et al. Cancer Biology and Therapy. 2005. 4: 440-448.*
Battagli et al. Cancer Research. Dec. 2003. 63: 8695-8699.*
Chow et al. Biomedicine and Pharmacotherapy. 2005. 59: S264-S267.*
Ehrlich et al. (Oncogene 2002. 21: 5400-5413.*
Nimmrich et al. Breast Cancer Research and Treatment. 2008. 111:429-437.*
Watanabe et al. Anticancer Research. 2003. 23(4): 3215-3221.*
Buchanan et al, "*RN: Connecting COX-2 and Wnt in Cancer*," Cancer Cell, 9:6-8 (2006).
Buskens et al, "*Comparison of Cyclooxygenase 2 Expression in Adenocarcinomas of the Gastric Cardia and Distal Oesophagus*," Gut. 52:1678-1683 (2003).
Hartgrink et al, "*Neo-Adjuvant Chemotherapy for Operable Gastric Cancer: Long Term Results of the Dutch Randomised FAMTX Trial*," EJSO, 30:643-649 (2004).

Huang et al, "*Infrequent COX-2 Expression Due to Promoter Hypermethylation in Gastric Cancers in Dalian, China*," Human Pathology 37:1557-1567 (2006).
Hur et al, "*Aberrant Methylation of the Specific CpG Island Portion Regulates Cyclooxygenase-2 Gene Expression in Human Gastric Carcinomas*," Biochemical and Biophysical Research Communications, 310:844-851 (2003).
Kang et al, "*Aberrant CpG island Hypermethylation of Chronic Gastritis, in Relation to Aging, Gender, Intestinal Metaplasia, and Chronic Inflammation*," American Journal of Pathology, 163:1551-1556 (2003).
Kang et al, "*Profile of Aberrant CpG Island Methylation Along the Multistep Pathway of Gastric Carcinogenesis*," Laboratory Investigation, 83:635-641 (2003).
Leung et al, "*Cyclooxygenase-2 Upregulates Vascular Endothelial Growth Factor Expression and Angiogenesis in Human Gastric Carcinoma*," International Journal of Oncology, 23:1317-1322 (2003).
Mrena et al, "*Cyclooxygenase-2 Is an Independent Prognostic Factor in Gastric Cancer and its Expression is Regulated by the Messenger RNA Stability Factor HuR*," Clinical Cancer Research, 11:7362-7368 (2005).
Murata et al, "*Cyclooxygenase-2 Overexpression Enhances Lymphatic Invasion and Metastasis in Human Gastric Carcinoma*," American Journal of Gastroenterology, 94:451-455 (1999).
Regalo et al, "*C/EBPbeta is Over-Expressed in Gastric Carcinogenesis and is Associated with COX-2 Expression*,". Journal of Pathology, 210:398-404 (2006).
Ristimaki et al, "*Expression of Cyclooxygenase-2 in Human Gastric Carcinoma*," Cancer Research, 57:1276-1280 (1997).
Tatsuguchi et al, "*Cyclooxygenase-2 Expression Correlates with Angiogenesis and Apoptosis in Gastric Cancer Tissue*," Human Pathology, 35:488-495 (2004).
Toyota et al, "*Aberrant Methylation in Gastric Cancer Associated with the CpG Island Methylator Phenotype*," Cancer Research, 59:5438-5442 (1999).
Wang et al, "*Mechanism and Clinical Significance of Cyclooxygenase-2 Expression in Gastric Cancer*," World J. Gastroenterol, 11:3240-3244 (2005).
PCT International Search Report, mailing date Sep. 9, 2008.
Ma et al., "*Promoter Methylation Regulates Cyclooxygenase Expression in Breast Cancer*," Breast Cancer Res., pp. R316-R321 (2004).
Murata et al., "*Promoter Hypermethylation Silences Cyclooxygenase-2 (Cox-2) and Regulates Growth of Human Hepatocellular Carcinoma Cells*," Lab Invest., 84, pp. 1050-1059 (2004).
Song et al., "*Transcriptional Silencing of Cyclooxygenase-2 by Hyper-Methylation of the 5' CpG Island in Human Gastric Carcinoma Cells*," Cancer Research, 61, pp. 4628-4635 (2001).

* cited by examiner

*Primary Examiner*—Carla Myers
(74) *Attorney, Agent, or Firm*—Perkins Coie LLP

(57) ABSTRACT

The present invention discloses methods of using the methylation status of the COX-2 gene promoter region as a biomarker for a gastric cancer patient to determine a prognosis and a treatment regimen, and to monitor the progress of a treatment regimen.

9 Claims, 9 Drawing Sheets

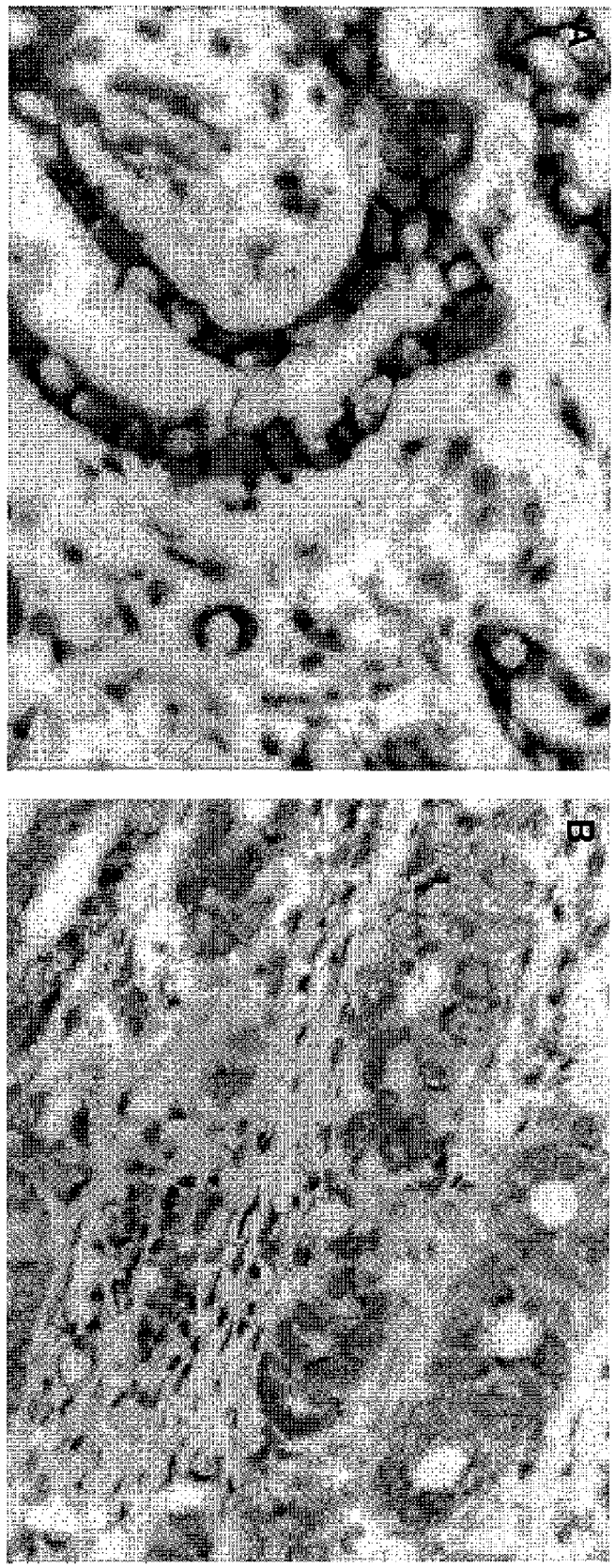
Figure 2 A – B

EPIGENETIC SILENCING OF CYCLOOXYGENASE-2 AFFECTS CLINICAL OUTCOME IN GASTRIC CANCER

CROSS-REFERENCE TO RELATED APPLICATIONS

This application claims the benefit of U.S. Provisional Application Ser. No. 60/943,812, filed Jun. 13, 2007, entitled "EPIGENETIC SILENCING OF CYCLOOXYGENASE-2 AFFECTS CLINICAL OUTCOME IN GASTRIC CANCER". The benefit under 35 USC §119(e) of the United States provisional application is hereby claimed. The above priority application is hereby incorporated herein by reference.

STATEMENT OF FEDERALLY SPONSORED RESEARCH AND DEVELOPMENT

The present invention is made, at least in part, with the support of grants from Department of Health and Human Services (AG11833, AG11644). The government has certain rights in the invention.

FIELD OF THE INVENTION

The present invention relates in general to cancer. More specifically, the invention provides methods of predicting disease outcome in gastric cancer patients based on the methylation status of the Cox-2 gene promoter region.

SEQUENCE LISTING

The present invention contains sequence listing.

BACKGROUND OF THE INVENTION

Gastric cancer has been and remains the second most common cause of cancer death and the third most common cancer worldwide [1]. Recently, gastric cancer therapy has received more attention, since neoadjuvant modalities have shown to improve outcome for respectable tumors [2-4]. In this respect, molecular surrogate marker(s) of disease outcome could be of benefit in the management of gastric cancer patient treatment. Furthermore, because gastric cancer is relatively resistant to chemotherapeutic agents, prognostic molecular determinants in gastric cancer could help improve adjuvant regimens.

About 60% of human genes are associated with clusters of CpG dinucleotides, referred to as CpG islands [5]. Clustered methylation of CpG islands at a gene promoter or transcription start site is associated with gene silencing. This epigenetic event has been observed in many genes of different cancers [6]. Hypermethylation of tumor-related regulatory genes may play a significant role in tumor transformation and progression, impacting the clinical course of disease. Several recent studies have focused on hypermethylation of specific tumor-related genes which appears to suppress growth and proliferation of gastric cancer [7-11]. Genes regulated by methylation status can significantly alter tumor suppressor functions as well as tumor-inducing capacities. Therefore, gene inactivation by hypermethylation may have dual effects on tumorigenesis and tumor progression.

To date, epigenetic inactivation of genes related with tumor progression has not been well studied in gastric cancer as related to disease outcome.

SUMMARY OF THE INVENTION

The present invention is based on the unexpected discovered that hypermethylation of cyclooxygenase-2 (COX-2) promoter is an independent favorable prognostic factor in gastric cancer patients. Based on this discovery, inventors of the present invention have devised methods for determining a prognosis for gastric cancer patients and methods for determining a course of treatment for the patients.

In accordance with embodiments of the present invention, methods for determining a prognosis for a cancer patient in accordance with embodiments of the present invention will generally include the steps of: obtaining a tumor tissue from the patient; extracting genomic DNA from the tissue sample; and determining the methylation status of the DNA for a predetermined number of base-pairs around the COX-2 promoter, wherein hypermethylation in the COX-2 promoter region indicates a positive prognosis.

Methods for determining a treatment course for a cancer patient in accordance with embodiments of the present invention will generally have the steps of: obtaining a tumor tissue sample from the patient; analyzing the sample to determine a methylation status in the COX-2 promoter region with a predetermined number of base-pairs around the promoter; and prescribing a course of treatment for the patient depending on the status of methylation.

Methods for monitoring the progress of a treatment for a cancer patient will generally have the steps of: obtaining a tumor tissue sample at the beginning of the treatment and determining the methylation status in the COX-2 promoter region with a predetermined number of base-pairs around the promoter to establish a baseline; obtaining a gastric tumor tissue sample at predetermined intervals and determining for each sample the methylation status in the COX-2 promoter region with a predetermined number of base-pairs around the promoter; and comparing the methylation status of the samples to determine a progress status for the treatment.

Other aspects and advantages of the invention will be apparent from the following description and the appended claims.

DETAILED DESCRIPTION

Figure 1:
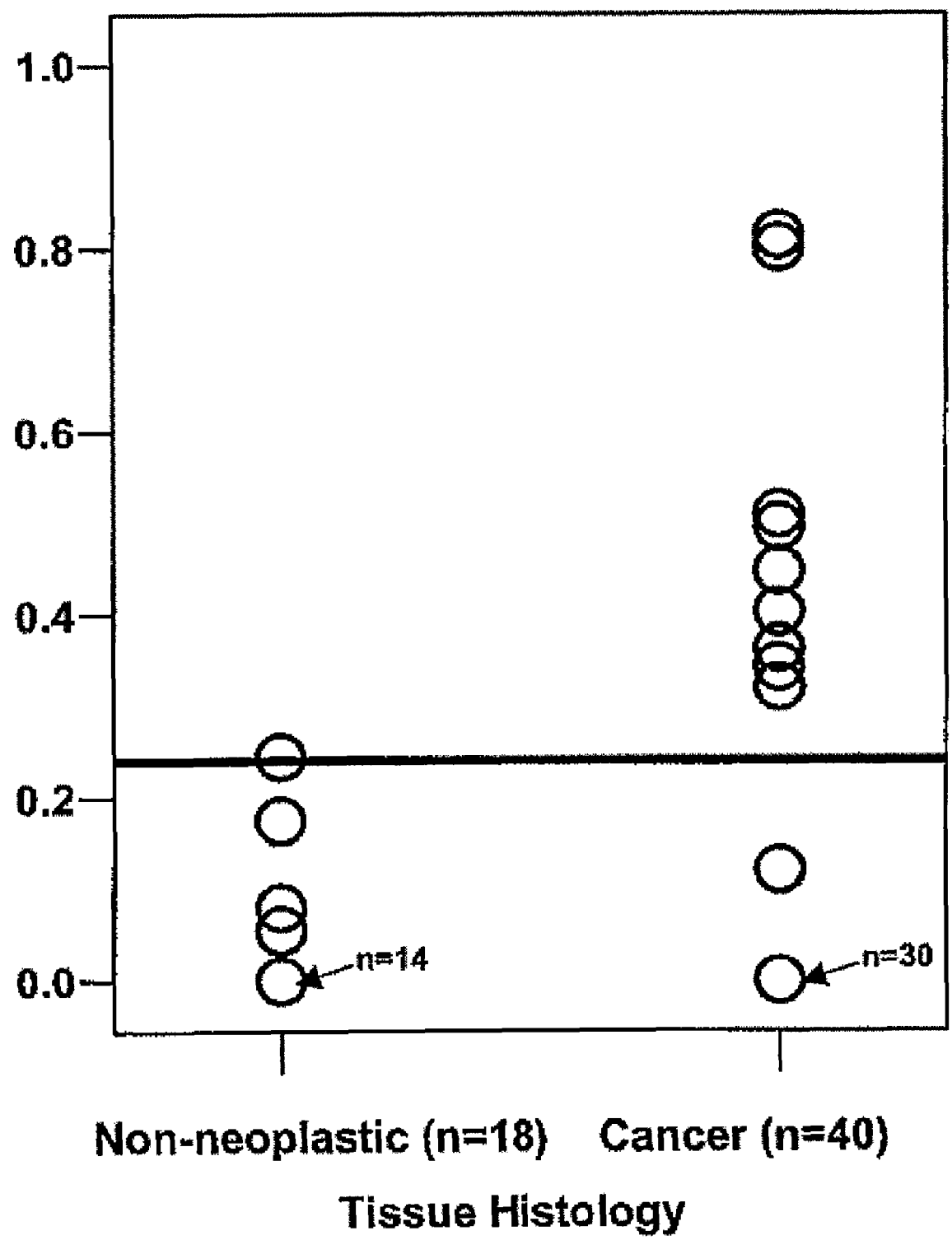
FIG. 1 shows a scatter plot indicating distribution of measured MI values in normal gastric epithelium and primary gastric tumor. Horizontal bar indicates the cut-off level for increased tumor-related methylation (MI=0.24).
Figure 2:
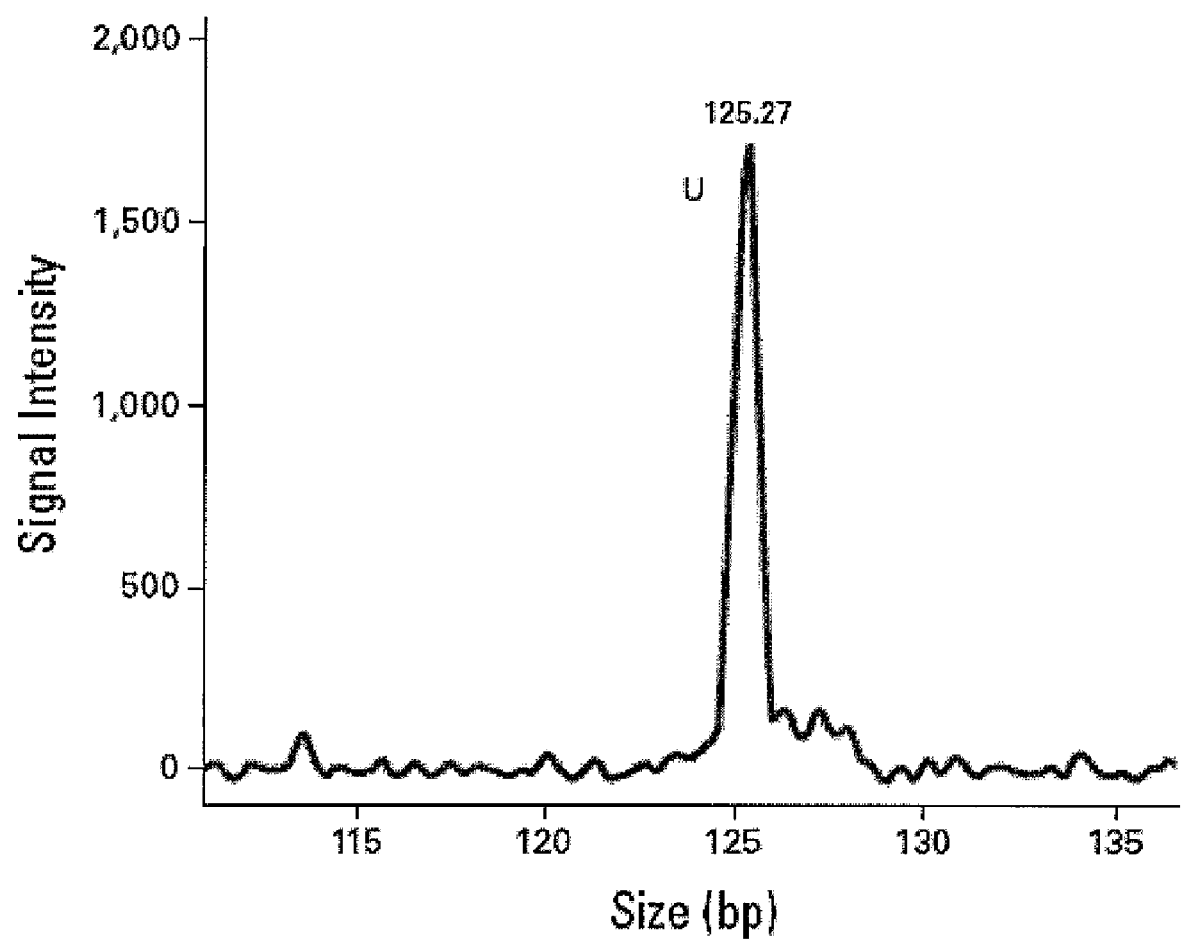
FIG. 2 shows representative COX-2 IHC results of primary gastric tumors with their respective MSP outcomes. The vertical axis of the MSP result represents the fluorescent intensity (M=methylated product, U=unmethylated product) indicating the amount of PCR amplicon and the horizontal axis represent the product size in basepairs. A, C, primary gastric tumor determined as unmethylated by MSP. Strong cytoplasmic staining in tumor cells represents COX-2 protein. B, D, Primary gastric tumors determined as methylated by MSP and tumor cells show weak diffuse IHC staining.
Figure 2:
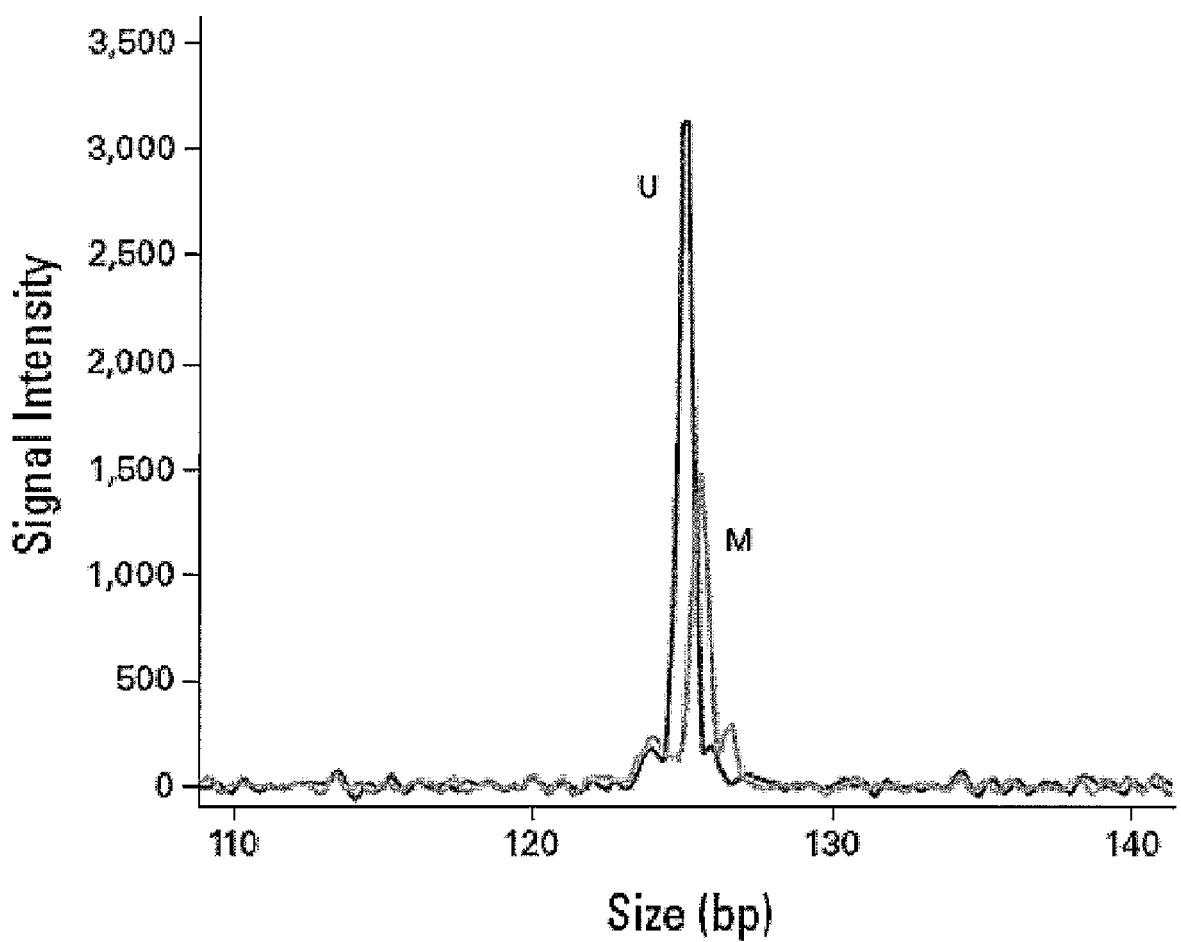
Figure 3:
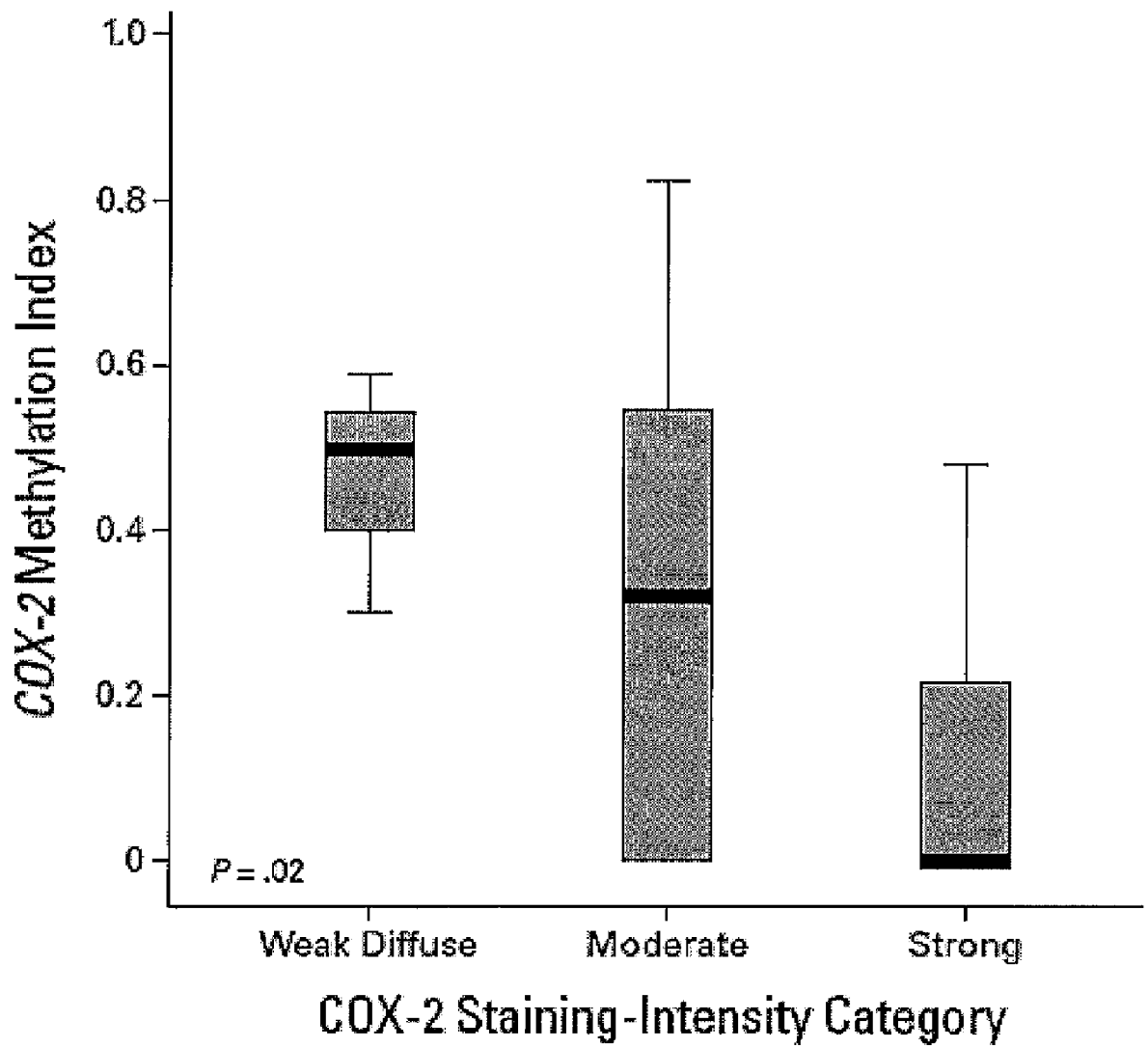
FIG. 3 shows boxplots illustrating gastric primary tumor COX-2 methylation index (Y-axis) in relation to COX-2 protein expression categories (X-axis) as assessed by IHC in gastric tumor cells.

COX-2 (cyclooxygenase-2/PTGS2, prostaglandin-endoperoxide synthetase-2) expression is upregulated in gastrointestinal cancers [12-15]. In gastric cancer, COX-2 expression is involved in several important tumor progression-related mechanisms, such as angiogenesis [1,6], inhibition of apoptosis [1,7], and invasiveness [1,8]. Song et al. demonstrated regulation of COX-2 mRNA and protein expression by hypermethylation of the COX-2 promoter region in gastric cancer lines [1,9]. Most gastric cancers overexpress COX-2, and, recently, COX-2 expression assessed by immunohistochemistry (IHC) was identified to impact disease survival [20]. Because of the reported epigenetic regulation and predictive value of COX-2 expression, we hypothesized a role for COX-2 promoter hypermethylation status in the clinical outcome of patients with gastric cancer. In making the discovery of the present invention, we first assessed COX-2 promoter methylation status by quantitative specific PCR (MSP), as well as its relation to COX-2 protein expression in paraffin-embedded archival tumor (PEAT) specimens of gastric cancer patients with known disease outcome in a pilot study. All patients were enrolled in a randomized, multi-center trial for primary gastric cancer comparing preoperative chemotherapy versus surgery alone [21, 22]. The clinical impact of COX-2 methylation in the cancer trial patients was studied by correlating disease outcome to tumor COX-2 methylation status. The MSP findings were then confirmed in a larger, independent validation patient group, selected from another multi-center randomized trial comparing primary tumor resection with limited versus extended nodal dissection [23, 24].

COX-2 methylation was detected in 23% and 28% of the pilot and validation patient groups, respectively. COX-2 expression (IHC) in gastric tumors inversely correlated with COX-2 gene methylation status in the pilot study (P=0.02). COX-2 methylation in tumors was significantly associated with lower T-, N-, and TNM-stage in the validation patient group (P=0.02, P=0.006 and P=0.008, respectively). Patients with COX-2 methylated tumors had significantly longer time to recurrence (TTR) and improved overall survival (OS) in a multivariate analysis in the smaller (HR=0.08; 95% CI, 0.01-0.65 and HR=0.37; 95% CI, 0.14-1.00, respectively) and larger patient groups (HR=0.49; 95% CI, 0.24-0.99 and HR=0.62; 95% CI, 0.38-0.99, respectively).

Hypermethylation of COX-2 gene promoter was identified as an independent favorable prognostic factor in gastric cancer patients. The results suggest that promoter hypermethylation is an important regulatory mechanism of COX-2 expression in gastric cancer. COX-2 downregulation is advocated as a potential target for adjuvant treatment in gastric cancer. Based on the above unexpected discovery of the present invention) the inventors have devised various methods disclosed herein.

In general, the present invention discloses methods of using the methylation status of the COX-2 gene promoter region as a biomarker in assessment of gastric cancer patients for determining a diagnosis, prognosis, prediction; determining a course of treatment; and monitoring the progress of a therapeutic regimen.

Methods for determining a prognosis for a cancer patient in accordance with embodiments of the present invention will generally include the steps of: obtaining a tissue from the patient; extracting genomic DNA from the tissue sample; and determining the methylation status of the DNA for a predetermined number of base-pairs around the COX-2 promoter, wherein hypermethylation in the COX-2 promoter region indicates a positive prognosis.

Any commonly known methods for obtaining tumor tissue from the patient may be suitably used. For example, tumor tissues may be obtained from excisional biopsy, needle aspirational biopsy, or a combination thereof. Preferably, tumor tissues are obtained by conventional surgery of primary tumor, endoscopy surgery. The biopsied samples are preferably processed prior to analysis. The means by which samples are processed are not particularly limited. Any types of tissue sample processing/preparation techniques commonly known in the art may be used. Preferably, collected samples may be analyzed fresh or may be frozen, paraffin-embedded; affixed by blood, stool, gastric fluid, or any form of tissue fixation.

Once a sample is successfully obtained, analysis of the sample may require extraction of the DNA from the sample. A number of commercial DNA extraction kits are available, however, any methods of DNA extraction commonly known in the art may be suitably used.

Determination of the methylation status is preferably performed using bisulfite conversion-based assays. Again, there are a number of commercially available tool kits for performing DNA methylation analysis, however, any methylation analysis methods commonly known in the art may all be suitably used.

Once the methylation status is determined, determination of a prognosis for the patient is straight forward. Exemplary prognosis may include a disease outcome, survival or disease free, response to treatment, or aggressive disease.

Methods for determining a treatment course for a cancer patient in accordance with embodiments of the present invention will generally have the steps of: obtaining a tumor tissue sample from the patient; analyzing the sample to determine a methylation status in the COX-2 promoter region with a predetermined number of base-pairs around the promoter; and prescribing a course of treatment for the patient depending on the status of methylation.

There is no particular limitation on the range of treatment regimen that may be suitable candidate for selection by this method. Any commonly known treatment regimen may be included as a potential candidate to be selected. The actual treatment regimen selected will depend on a number of factors, but mainly on the status of methylation at the region around COX-2 promoter for about −14 bp/+110 bp. Methods for obtaining a tumor sample and analyzing methylation status are as described above. Any commonly known methods for analyzing DNA methylation may also be suitably used. Exemplary methods for DNA methylation may include assessment by capillary array electrophoresis (CAE), real time PCR, mass spectrometry (such as MALDI-TOF), any form of direct sequencing, gel electrophoresis, digital analysis, optical sequencing, antibody/analog binding molecule based assay, microarrays, etc, but are not limited thereto. In one exemplary embodiment, when a hypomethylation status is determined, a currently accepted adjuvant therapy is prescribed. Alternatively, further exploratory surgery is performed to identify disease spread. Other regimens that may be prescribed may include giving the patient a preventative treatment to prevent recurrence or progression treatment regimen.

In another preferred embodiment, when a patient is diagnosed with hypomethylation, a targeted treatment may be prescribed. Exemplary targeted treatment may include administering to the patient a COX-2 inhibitor or an inhibitor for down-stream molecule.

The identification of hypomethylation of COX-2 promoter region can also be used to assess for benign lesions or suspicious lesions for developing into cancer. Thus, in another preferred embodiment, when a patient having a benign tumor, adenoma or hyperplasia is diagnosed as being hypomethylated in the COX-2 promoter region, further exploratory surgery or preventative treatment such as a COX-2 inhibitor or downstream pathway molecule inhibitor may be prescribed.

Methods for monitoring the progress of a treatment for a cancer patient will generally have the steps of: obtaining a tumor tissue sample at the beginning of the treatment and determining the methylation status in the COX-2 promoter region with a predetermined number of base-pairs around the promoter to establish a baseline; obtaining a tumor tissue sample at predetermined intervals and determining for each sample the methylation status in the COX-2 promoter region with a predetermined number of base-pairs around the promoter; and comparing the methylation status of the samples to determine a progress status for the treatment.

Methods of the present invention are not only applicable to gastric cancer, but may also be extended to other forms of cancer. Exemplary cancers that may benefit from methods of the present invention may include breast, melanoma, renal cancer, prostate, and gastrointestinal cancers, but are not limited thereto.

Having generally described this invention, a further understanding can be obtained by reference to certain specific examples which are provided herein for purposes of illustration only and are not intended to be limiting unless otherwise specified.

EXAMPLE

Materials and Methods

Tumor Specimen

The pilot study group contained patients (n=59) accrued in the FAMTX (5-fluorouracil, doxorubicin, and methotrexate) trial conducted by the Dutch Gastric Cancer Group (DGCC) [21, 22] evaluating preoperative chemotherapy with FAMTX for gastric cancer. As a validation set, patients were used from the D1D2 trial by the DGCC [23, 24]. The trial evaluated (sub)total gastrectomy for gastric cancer with D1 to D2 lymph node dissection of which the latter, included partial removal of spleen and pancreas. All tumors were classified and staged according to the revised guidelines set by the International Union Against Cancer (UICC). As tissue controls, PEAT specimens of the primary tumor were collected from patients from both trials. PEAT specimens from gastric tissue biopsies for benign conditions as controls were also collected from 18 patients without a history of malignancy. The protocol for this study was approved by the Human Subjects Institutional Review Boards of both participating institutions (Saint John's Health Center/JWCI; Leiden University Medical Center).

DNA Preparation

One 7-µm section from each PEAT specimen was cut, deparaffinized, and stained with hematoxylin. Tumor tissue was precisely isolated by manual microdissection under an inverted microscope. Isolated tissue was digested by 50 µl of proteinase K (Qiagen Inc, Valencia, Calif.) containing lysis buffer at 50° C. for 16 hrs. Subsequently, DNA was purified with phenol-chloroform-isoamyl alcohol (Fisher Chemicals, Fairlawn, N.J.), precipitated by ethanol and quantified by the PicoGreen assay for dsDNA (Molecular Probes, Eugene, Oreg.).

Analysis of CpG Island Methylation Status

Sodium bisulfite modification (SBM) was performed on PEAT DNA plus 1 µg of salmon sperm DNA as a carrier. SBM was carried out as previously described [25]; sulphonation incubation time was 3 hrs at 60° C. Methylation-specific and unmethylated-specific primer sets were designed around the COX-2 transcription start site (−14 bp/+110 bp). The primers were dye-labeled for detection using capillary array electrophoresis (CAE). Forward and reverse sequences for the methylation-specific primer set were: 5'-TTTCGGTTAGC-GATTAATTGTTATAC-3' (SEQ ID No.: 1) and 5'-CGAAAATAAACTTTACTATCTAAAAACGTC-3' (SEQ ID No.: 2), respectively. Forward and reverse sequences for the non-methylated-specific primer set were: 5'-TTTG-GTTAGTGATTAATTGTTATATGA-3' (SEQ ID No.: 3) and 5'-CAAAAATAAACTTTACTATCTAAAAACATC-3' (SEQ ID No.: 4), respectively. Controls and PCR conditions were used as previously reported [26]. Relative amounts of PCR products were quantified by CAE (CEQ 8000XL, Beckman Coulter, CA) using CEQ 8000XL software version 6.0 (Beckman Coulter), as described previously [27]. A methylation index (MI) was calculated; MI=[(methylated peak intensity)/(methylated peak intensity+unmethylated peak intensity)][28].

Immunohistochemistry

PEAT sections (4 µm) were prepared on aminopropylethoxysilane (APES) coated slides. Endogenous peroxidase was blocked by hydrogen peroxidase-methanol for 20 min. Antigen retrieval was performed by boiling the sections in 10 mM citrate buffer for 10 min. Sections were incubated overnight at room temperature with a monoclonal antibody against human COX-2 (Cayman Chemical, MI) at a dilution of 1:200 (2.5 µg/mL) in phosphate-buffered saline (pH 7.4) with 1% BSA (PBS/BSA). Sections were then incubated for 30 min with biotin (1:400; DAKO, Glustrup, Denmark), washed, and incubated for 30 min with Streptavidin-Biotin-Complex (SABC) (1:100; DAKO, Denmark). The sections were washed in PBS for 15 min, rinsed in Tris/HCl-buffer (pH 7.6) for 5 min, and developed in 3.3 diaminobenzidine tetrahydrochloride (DAB) with hydrogen-peroxide for 10 min. The sections were counterstained with hematoxylin and mounted. COX-2 IHC staining intensity of tumor cell cytoplasm was scored independently in a blinded manner by two expert gastric cancer pathologists (GAM and NCvG) using the following scoring criteria: absent staining; weak diffuse cytoplasmic staining (may contain stronger intensity in <10% of the cancer cells); moderate granular cytoplasmic staining in 10%-90% of the cancer cells; and strong granular staining in more than 90% of the tumor cells according to the method of Buskens et al., [29]. In case of disagreement, a third independent staining assessment (by PdH) was used to designate tumor staining-intensity.

MSP Assay Validation

Methylation status of the COX-2 promoter region was confirmed in gastric cancer lines, KATO-III (ATCC, Manassas, Va.) and FN-0028 (JWCI), by direct bisulfite sequencing, as described previously (28). Forward and reverse sequencing primers were 5'-TAAGGGGAGAGGAGGGAAAA-3' (SEQ ID No.: 5) and 5'-CACCTATATAACTAAACYC-CAAAACC-3' (SEQ ID No.: 6), respectively, with Y-A or G. Both cell lines were treated with 5-azacytidine (5-aza) and trichostatin-A (TSA) for verification of epigenetic regulation of COX-2 mRNA expression, as described previously [28, 30]. COX-2/GAPDH mRNA expression ratio was assessed by using quantitative RealTime PCR [31]. Sequences for forward and reverse primers and fluorescent labeled probe for COX-2 mRNA were 5'-CATTTGAAGAACTTACAGG-3'

(SEQ ID No.: 7), 5'-CCAAAGATGGCATCTG-3' (SEQ ID No.: 8), and 5'-FAM-CTCCACAGCATCGATGTCAC-CATA-BHQ-3' (SEQ ID No.: 9), respectively.

Study Design and Statistical Analyses

This was a retrospective study and all assays were performed in a blinded manner to the trial clinical outcome parameters. We first established tumor-specific MI by assessment of non-neoplastic gastric tissue controls. A cut-off MI to allocate tumors to the methylated or unmethylated category was set at the 95th percentile of the measured MI values in normal controls. This cut-off was uniformly and consistently used to study the clinical value of COX-2 methylation status initially in the pilot study and then in the validation D1D2 trial specimens. D1D2 trial patients that received resection with curative intent were selected, satisfying the following criteria: availability of primary tumor block, complete surgical resection (R0), and no postoperative mortality. Required sample size was calculated based on the prevalence of COX-2 methylation in the pilot study and the number of tumor recurrence events, accounting for a 25% loss of cases due to poor DNA quality. Correlation between methylation status of the COX-2 gene and clinicopathological features was analyzed by Fisher's exact test or Pearson's $\chi^2$ test. Student's t-test evaluated differences in age between groups. The Mann-Whitney U-test was used for ordinal variables. Survival length was determined from the day of primary tumor surgery to the date of death or last clinical follow-up. The Kaplan-Meier method was used for survival analysis grouping with COX-2 methylation status. Differences between curves were analyzed using the log-rank test. Cox's proportional hazard regression model was used in a backward stepwise method for variable selection in multivariate analyses. T-stage, N-stage, TNM-stage, trial randomization, Lauren classification, and complete resection were included in the model. Kruskal-Wallis test was used to assess the relation between COX-2 MI and the different staining-intensity categories. The statistical package SPSS version 12.0.1 (SPSS Inc, IL) was used; a value of P<0.05 (two-tailed) was considered significant.

Results

MSP Assay Validation

Regulation of COX-2 expression by promoter region methylation has previously been shown in gastric cancer lines [1,9]. We first verified whether our MSP assay on COX-2 methylation status associated with regulation of COX-2 mRNA expression. Two representative gastric cancer lines assessed as methylated (KATO-III) and unmethylated (FN-0028) by the MSP assay were treated by 5-aza and TSA to evaluate COX-2 mRNA re-expression. Methylation status of the promoter transcription site was confirmed by bisulfite sequencing. The combination of agents was used because epigenetic silencing can involve both methylation of CpG islands and deacetylation. In KATO-III, the demethylating effect was confirmed by MSP, and expression of COX-2 mRNA was induced (COX-2/GAPDH ratio was 0 versus 4.46E-02, respectively, before and after treatment). In FN-0028, COX-2 mRNA was present before treatment and did not significantly change after treatment (COX-2/GAPDH ratio was 1.69E-04 versus 3.45E-04, respectively). Results confirmed that promoter region methylation affects COX-2 expression, and validated the MSP assay for detecting methylation at the COX-2 promoter region transcription site.

Primary Tumor COX-2 Methylation Status

Increased COX-2 methylation has been shown to be a tumor-related event in gastric cancer [32, 33]. Using the COX-2 MSP assay, we verified tumor-related COX-2 levels. Methylation status was assessed in FAMTX patients' primary tumors, as well as 18 non-cancerous gastric biopsies in patients with benign conditions as controls. Forty-four of the 59 patients enrolled in the trial finally underwent resection. Three of the 44 primaries could not be evaluated because of insufficient DNA, and in one patient the paraffin-embedded block had an insufficient amount of cells, leaving 40 patients available for analysis. Relatively low levels of COX-2 methylation were detected in control samples compared to tumors (FIG. 1). The 95th percentile of the MI values in non-neoplastic gastric tissues was calculated (MI=0.24) and used as a cut-off to establish tumor-related methylation. COX-2 methylation was detected by the MSP assay in 9 of 40 (23%) tumors using the predetermined cut-off level standard.

COX-2 Methylation and Clinical Outcome

Figure 4A:
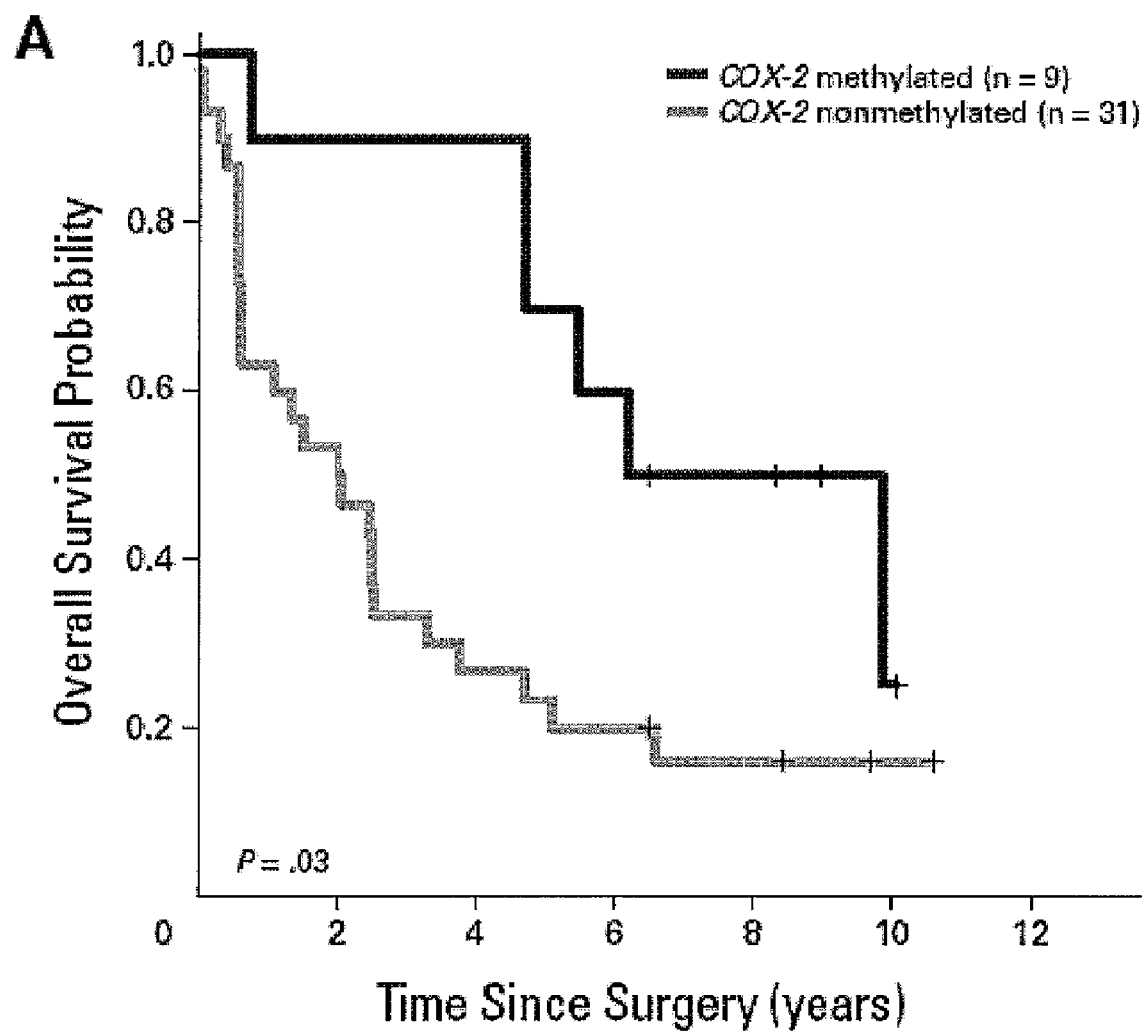
FIG. 4 shows Kaplan-Meier analysis of survival for gastric cancer patients with primary tumors assessed for methylation status of COX-2. Among 40 FAMTX trial patients, those with methylated primary tumors had a significantly improved overall survival (A) and longer time to recurrence for 35 patients that could be evaluated for this outcome parameter in B. C and D represent Kaplan-Meier analysis of 137 D1D2 trial gastric cancer patients (n=137).
Figure 4B:
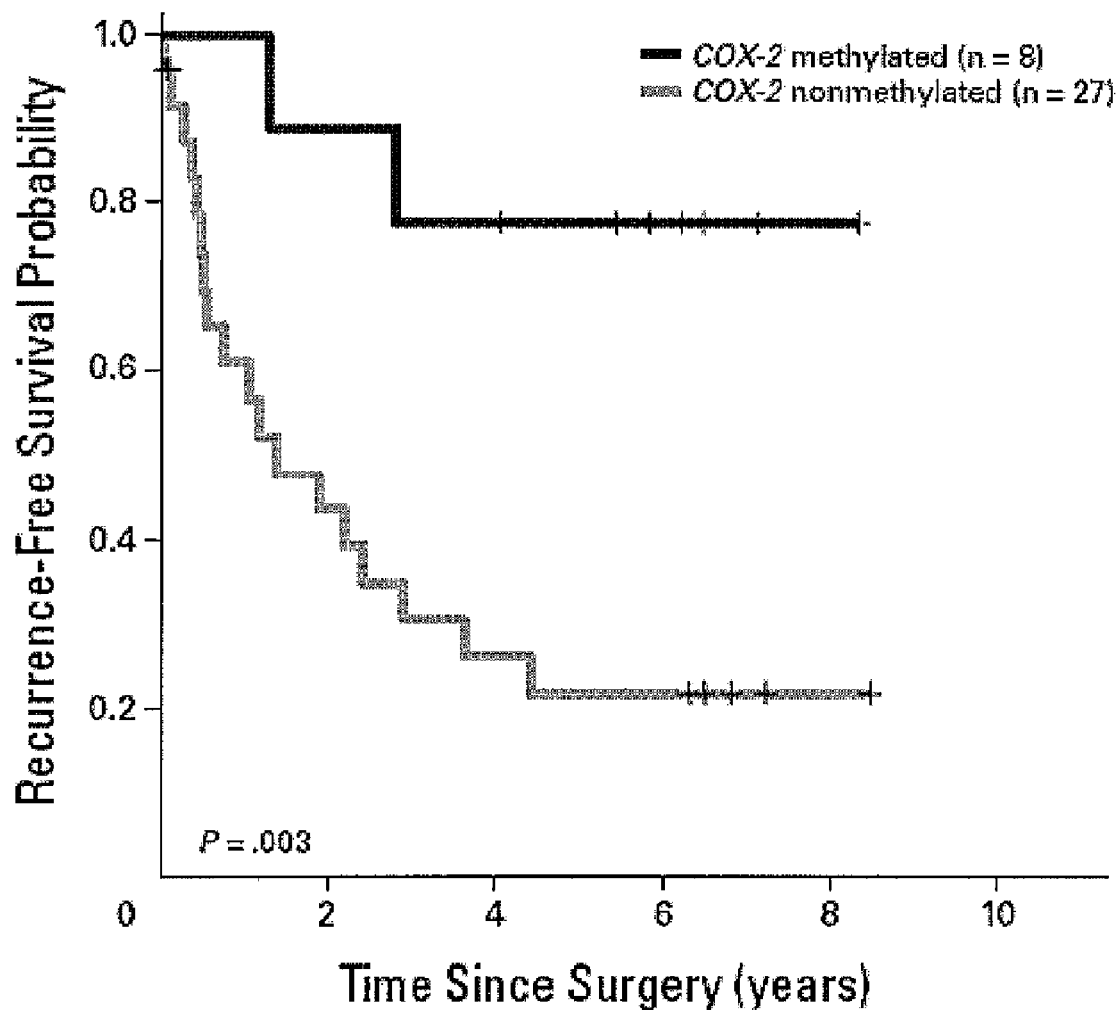
Figure 4C:
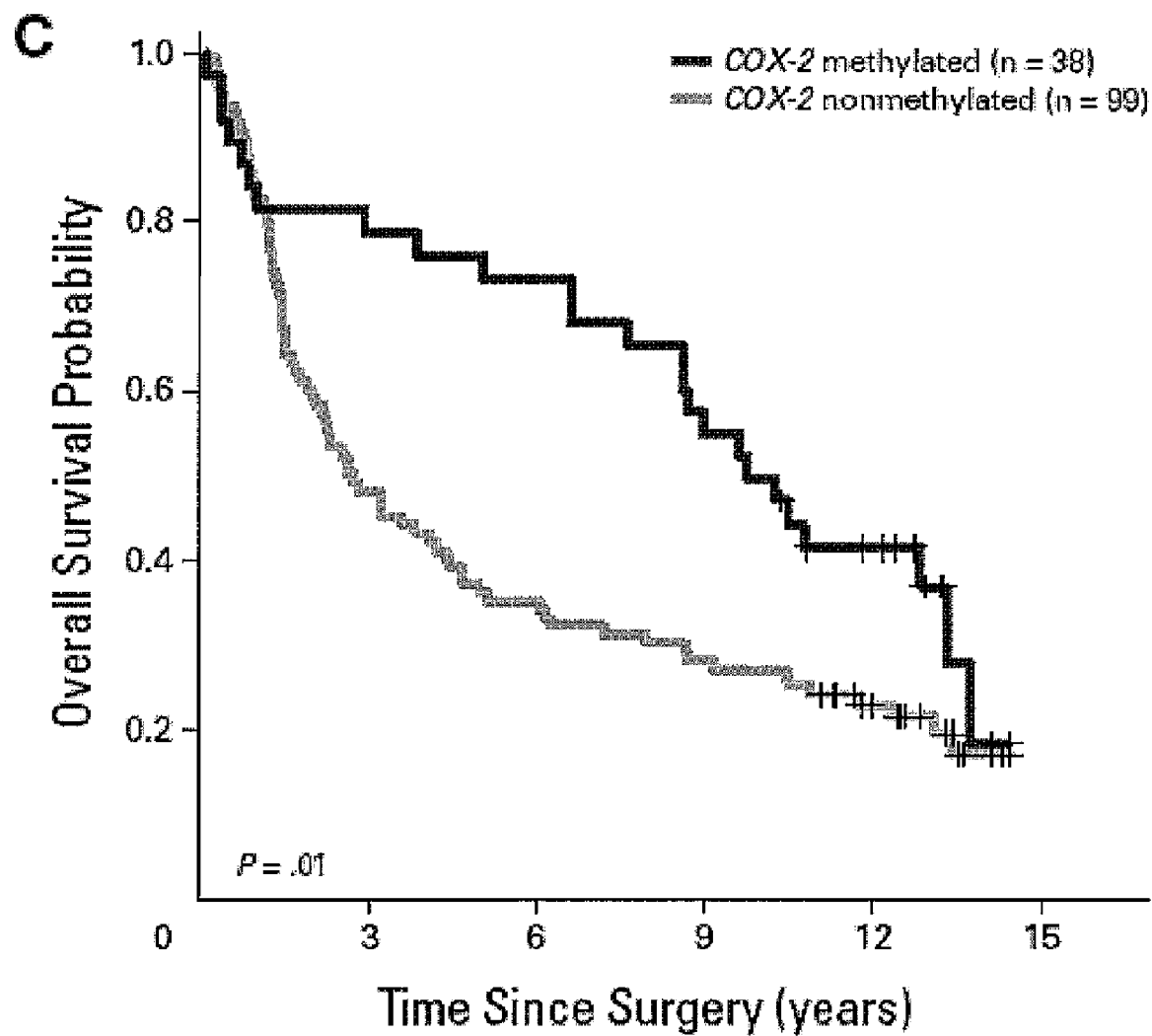
Figure 4D:
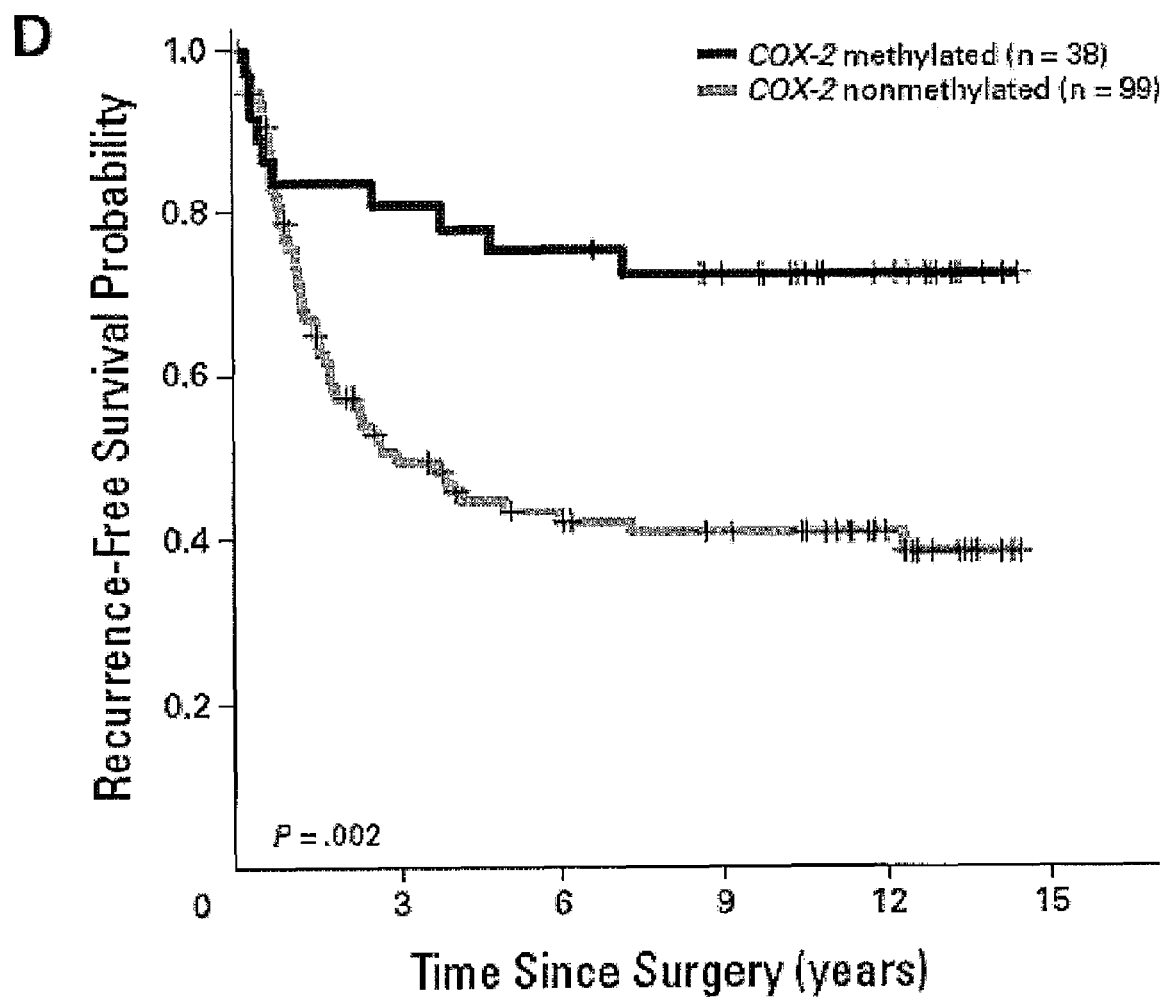

We evaluated gastric cancer patients' clinical prognostic factors between COX-2 methylated and non-methylated FAMTX trial tumors in a pilot study. COX-2 methylation status showed no relation to sex, age, Lauren type, T-, N- or TNM-stage, or respectability in this patient group (Table 1). Univariate analysis of Kaplan Meier survival curves (FIG. 4A-B) demonstrated that COX-2 methylation status gave significant differences in time to recurrence (TTR) and overall survival (OS). Five patients that did not receive a curative (R0) resection were excluded for the analysis of TTR. Multivariate analysis (Table 2) showed that methylation of the COX-2 gene was a favorable independent prognostic factor for TTR and OS. Nodal status showed the strongest predictive value, as expected. The multivariate analysis also showed predictive value for the FAMTX trial randomization arm, indicating improved outcome for patients that received surgery alone.

Discussion

Our study demonstrated, in two independent, multi-center patient populations, that promoter region hypermethylation of COX-2 is an independent prognostic factor for OS and TTR. After in vitro validation by MSP, we established tumor-related COX-2 methylation levels in a pilot study, and subsequently confirmed that gastric COX-2 protein expression was correlated to COX-2 methylation levels. COX-2 methylated tumors had significantly fewer recurrences, lower stage and invasion depth, and were more likely to be node-negative. This suggested that there may be a selection advantage of COX-2 methylated tumor cells, resulting in reduced potential of gastric tumors to grow out and spread to distant sites. In gastrointestinal cancers, the role of COX-2 in tumor-promotion has been shown [34, 35]. Numerous stimulatory factors, such as growth factors and cytokines, have been reported to cause overexpression of COX-2 in cancer [34, 36-38]. Studies have suggested methylation as a regulatory mechanism of COX-2 expression in gastric cancer in vitro and in primary tumors [19, 33, 39-41]. Recently it was reported that C/EBPbeta (CCAAT/enhancer-binding protein beta) transcription factor regulates the expression of endogenous COX-2 in a gastric cancer line model, based on its methylation status [42]. The COX-2 methylated status may abolish the effect of factors, such as C/EBPbeta, growth factors, or cytokines, due to the inactivation of binding elements at the promoter region. Our study is the first demonstrating clinical relevance of methylated COX-2 in gastric cancer. Also, this is one of the first studies in gastric cancer showing that tumor methylation of a gene can have favorable impact on clinical outcome.

Multivariate analyses of prognostic factors in the FAMTX trial indicated the negative impact of preoperative chemotherapy, probably due to low response rates to FAMTX and incomplete treatment because of high toxicity [21]. Although there was no correlation to trial randomization, and methylation status was an independent variable in multivariate analyses, we sought confirmation to corroborate the predictive value of COX-2 methylation in gastric cancer. In the D1D2 trial validation set, randomization did not correlate to methylation status and had no predictive value in multivariate analysis. Both trial study populations demonstrated strong predictive value of nodal status. Despite the significant correlation to nodal involvement, COX-2 methylation status was a significant independent predictive factor. This suggests that COX-2 acts on various events during the growth and metastatic processes. Our data suggests that COX-2 to be involved in Lauren's histologic classification. In the pilot study, intestinal type tumors correlated to decreased IHC staining intensity (P=0.03), and absence of COX-2 expression in the intestinal tumor type has been previously reported [20]. In the D1D2 trial patient group diffuse type tumors had a significantly decreased MI compared to intestinal type tumors (P=0.03). Together, methylation of COX-2 may cause gastric tumor cells to maintain a more differentiated, intestinal organization, and subsequently these tumors may constitute a clinically less aggressive tumor type.

The outcome of both trials, for which patient specimens were used in this study, was negative. The FAMTX trial did not show improved respectability rate of gastric cancer by preoperative chemotherapy, and extended D2 nodal dissection did not reduce recurrence rates, indicating the problem of managing gastric cancer disease. Development of molecular biomarkers for primary gastric cancer tumors may allow for better management strategies. Long-term analyses of the D1D2 trial suggested that node-positive gastric cancer patients may benefit from more extensive nodal dissection at primary tumor surgery [24], and two large randomized trials have now shown the benefit of (neo-) adjuvant treatment for gastric cancer [3,4]. Primary tumor COX-2 methylation status may be used as a preoperatively assessable biomarker to tailor more aggressive treatment modalities to gastric cancer patients with poorer prognosis. The significant contribution of COX-2 to postoperative tumor progression of gastric cancer suggests that COX-2 is a promising target for gastric cancer treatment in an adjuvant setting. Assessment of COX-2 methylation status of a primary gastric tumor may be used to identify patients likely to benefit from adjuvant therapy.

In summary, assays have been developed to assess COX-2 promoter region methylation status by methylation specific PCR in gastric cancer tumors. Hypermethylation in primary tumor predicts significant disease outcome in long term follow up. Assessment carried out on paraffin-embedded (PE) tissues. Methylation specific PCR performed followed by capillary array electrophoresis (CAE). Such assays can be used to determine prognosis of patient at time of primary tumor surgery for gastric cancer, to stratify patients for anti-COX 2 inhibiting drugs such as asprin, celecoxib (sold under the trademark CELEBREX®), etc., and to stratify patients for other drugs. Hypomethylation of COX-2 indicates more aggressive tumor.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

All cited publications are incorporated by reference in their entirety.
1. Dicken B J, Bigam D L, Cass C, et al: Gastric adenocarcinoma: review and considerations for future directions. Ann Surg 241:27-39, 2005.
2. Macdonald J S: Gastric cancer—new therapeutic options. N Engl J Med 355:76-7, 2006.
3. Macdonald J S, Smalley S R, Benedetti J, et al: Chemoradiotherapy after surgery compared with surgery alone for adenocarcinoma of the stomach or gastroesophageal junction. N Engl J Med 345:725-30, 2001.
4. Cunningham D, Allum W H, Stenning S P, et al: Perioperative chemotherapy versus surgery alone for respectable gastroesophageal cancer. N Engl J Med 355:11-20, 2006.
5. Bird A: DNA methylation patterns and epigenetic memory. Genes Dev 16:6-21, 2002.
6. Jones P A, Baylin S B: The fundamental role of epigenetic events in cancer. Nat Rev Genet. 3:415-28, 2002.
7. Toyota M, Ahuja N, Suzuki H, et al: Aberrant methylation in gastric cancer associated with the CpG island methylator phenotype. Cancer Res 59:5438-42, 1999.
8. Byun D S, Lee M G, Chae K S, et al: Frequent epigenetic inactivation of RASSF1A by aberrant promoter hypermethylation in human gastric adenocarcinoma. Cancer Res 61:7034-8, 2001.
9. Li Q L, Ito K, Sakakura C, et al: Causal relationship between the loss of RUNX3 expression and gastric cancer. Cell 109:113-24, 2002.
10. Park T J, Han S U, Cho Y K, et al: Methylation of O(6)-methylguanine-DNA methyltransferase gene is associated significantly with K-ras mutation, lymph node invasion, tumor staging, and disease free survival in patients with gastric carcinoma. Cancer 92:2760-8, 2001.
11. Graziano F, Arduini F, Ruzzo A, et al: Prognostic analysis of E-cadherin gene promoter hypermethylation in patients with surgically resected, node-positive, diffuse gastric cancer. Clin Cancer Res 10:2784-9, 2004.
12. Eberhart C E, Coffey R J, Radhika A, et at: Up-regulation of cyclooxygenase 2 gene expression in human colorectal adenomas and adenocarcinomas. Gastroenterology 107: 1183-8, 1994.
13. Ristimaki A, Honkanen N, Jankala H, et al: Expression of cyclooxygenase-2 in human gastric carcinoma. Cancer Res 57:1276-80, 1997.
14. Zimmermann K C, Sarbia M, Weber A A, et al: Cyclooxygenase-2 expression in human esophageal carcinoma. Cancer Res 59:198-204, 1999.
15. Tucker O N, Dannenberg A J, Yang E K, et al: Cyclooxygenase-2 expression is up-regulated in human pancreatic cancer. Cancer Res 59:987-90, 1999.
16. Leung W K, To K F, Go M Y, et al: Cyclooxygenase-2 upregulates vascular endothelial growth factor expression and angiogenesis in human gastric carcinoma. Int J Oncol 23:1317-22, 2003.
17. Tatsuguchi A, Matsui K, Shinji Y, et al: Cyclooxygenase-2 expression correlates with angiogenesis and apoptosis in gastric cancer tissue. Hum Pathol 35:488-95, 2004.
18. Murata H, Kawano S, Tsuji S, et al: Cyclooxygenase-2 overexpression enhances lymphatic invasion and metastasis in human gastric carcinoma. Am J Gastroenterol 94:451-5, 1999.

19. Song S H, Jong H S, Choi H H, et al: Transcriptional silencing of Cyclooxygenase-2 by hyper-methylation of the 5' CpG island in human gastric carcinoma cells. Cancer Res 61:4628-35, 2001.
20. Mrena J, Wiksten J P, Thiel A, et al: Cyclooxygenase-2 is an independent prognostic factor in gastric cancer and its expression is regulated by the messenger RNA stability factor. HuR. Clin Cancer Res 11:7362-8, 2005.
21. Hartgrink H H, van de Velde C J, Putter H, et al: Neoadjuvant chemotherapy for operable gastric cancer: long term results of the Dutch randomised FAMTX trial. Eur J Surg Oncol 30:643-9, 2004.
22. Songun I, Keizer M J, Hermans J, et al: Chemotherapy for operable gastric cancer: results of the Dutch randomised FAMTX trial. The Dutch Gastric Cancer Group (DGCG). Eur J Cancer 35:558-62, 1999.
23. Bonenkamp J J, Hermans J, Sasako M, et al: Extended lymph-node dissection for gastric cancer. N Engl J Med 340:908-14, 1999.
24. Hartgrink H H, van de Velde C J, Putter H, et al: Extended lymph node dissection for gastric cancer: who may benefit? Final results of the randomized Dutch gastric cancer group trial. J Clin Oncol 22:2069-77, 2004.
25. Spugnardi M, Tommasi S, Dammann R, et al: Epigenetic inactivation of RAS association domain family protein 1 (RASSF1A) in malignant cutaneous melanoma. Cancer Res 63:1639-43, 2003.
26. Umetani N, de Maat M F, Mori T, et al: Synthesis of universal unmethylated control DNA by nested whole genome amplification with phi29 DNA polymerase. Biochem Biophys Res Commun 329:219-23, 2005.
27. Hoon D S, Spugnardi M, Kuo C, et al: Profiling epigenetic inactivation of tumor suppressor genes in tumors and plasma from cutaneous melanoma patients. Oncogene 23:4014-22, 2004.
28. Umetani N, Takeuchi H, Fujimoto A, et al: Epigenetic inactivation of ID4 in colorectal carcinomas correlates with poor differentiation and unfavorable prognosis. Clin Cancer Res 10:7475-83, 2004.
29. Buskens C J, Sivula A, van Rees B P, et al: Comparison of cyclooxygenase 2 expression in adenocarcinomas of the gastric cardia and distal oesophagus. Gut 52:1678-83, 2003.
30. Mori T, Kim J, Yamano T, et al: Epigenetic up-regulation of C—C chemokine receptor 7 and C—X—C chemokine receptor 4 expression in melanoma cells. Cancer Res 65:1800-7, 2005.
31. Takeuchi H, Kuo C, Morton D L, et al: Expression of differentiation melanoma-associated antigen genes is associated with favorable disease outcome in advanced-stage melanomas. Cancer Res 63:441-8, 2003.
32. Kang G H, Lee H J, Hwang K S, et al: Aberrant CpG island hypermethylation of chronic gastritis, in relation to aging, gender, intestinal metaplasia, and chronic inflammation. Am J Pathol 163:1551-6, 2003.
33. Kang G H, Lee S, Kim J S, et al: Profile of aberrant CpG island methylation along the multistep pathway of gastric carcinogenesis. Lab Invest 83:635-41, 2003.
34. Buchanan F G, DuBois R N: Connecting COX-2 and Wnt in cancer. Cancer Cell 9:6-8, 2006.
35. Williams C, Shattuck-Brandt R L, DuBois R N: The role of COX-2 in intestinal cancer. Ann N Y Acad Sci 889:72-83, 1999.
36. Buchanan F G, Chang W, Sheng H, et al: Up-regulation of the enzymes involved in prostacyclin synthesis via Ras induces vascular endothelial growth factor. Gastroenterology 127:1391-400, 2004.
37. Coffey R J, Hawkey C J, Damstrup L, et al: Epidermal growth factor receptor activation induces nuclear targeting of cyclooxygenase-2, basolateral release of prostaglandins, and mitogenesis in polarizing colon cancer cells. Proc Natl Acad Sci USA 94:657-62, 1997.
38. Dannenberg A J, Lippman S M, Mann J R, et al: Cyclooxygenase-2 and epidermal growth factor receptor: pharmacologic targets for chemoprevention. J Clin Oncol 23:254-66, 2005.
39. Wang B C, Guo C Q, Sun C, et al: Mechanism and clinical significance of cyclooxygenase-2 expression in gastric cancer. World J Gastroenterol 11:3240-4, 2005.
40. Hur K, Song S H, Lee H S, et al: Aberrant methylation of the specific CpG island portion regulates cyclooxygenase-2 gene expression in human gastric carcinomas. Biochem Biophys Res Commun 310:844-51, 2003.
41. Huang L, Zhang K L, Li H, et al: Infrequent COX-2 expression due to promoter hypermethylation in gastric cancers in Dalian, China. Hum Pathol, 2006.
42. Regalo G, Canedo P, Suriano O, et al: C/EBPbeta is over-expressed in gastric carcinogenesis and is associated with COX-2 expression. J Pathol, 2006.

TABLE 1

Association among COX-2 methylation and clinicopathological variables

| | FAMTX trial patients (n = 40) | | | D1D2 trial patients (n = 137) | | |
|---|---|---|---|---|---|---|
| | COX-2 | | | COX-2 | | |
| | Meth n = 9 | Unmeth n = 31 | P-value | Meth n = 38 | Unmeth n = 99 | P-value |
| Sex | | | | | | |
| Female | 5 | 15 | 0.84 | 19 | 47 | 0.79 |
| Male | 4 | 16 | | 19 | 52 | |
| Age | | | | | | |
| mean ± SD | 61.7 ± 6.6 | 60.1 ± 9.9 | 0.58* | 66.9 ± 8.7 | 67.2 ± 8.2 | 0.85* |

TABLE 1-continued

Association among COX-2 methylation and clinicopathological variables

| | FAMTX trial patients (n = 40) | | | D1D2 trial patients (n = 137) | | |
|---|---|---|---|---|---|---|
| | COX-2 | | | COX-2 | | |
| | Meth n = 9 | Unmeth n = 31 | P-value | Meth n = 38 | Unmeth n = 99 | P-value |
| Randomization | | | | | | |
| FAMTX + surgery/D1 resection | 4 | 15 | 0.84 | 24 | 54 | 0.36 |
| Surgery alone/D2 resection | 5 | 16 | | 14 | 45 | |
| Lauren Classification | | | | | | |
| Intestinal | 6 | 17 | 0.59 | 33 | 73 | 0.34 |
| Diffuse | 3 | 14 | | 4 | 23 | |
| Mixed | — | — | | 1 | 3 | |
| Pathologic Stage (UICC) | | | | | | |
| IA | 2 | 2 | 0.43† | 15 | 14 | 0.008† |
| IB | 2 | 5 | | 8 | 23 | |
| II | 2 | 15 | | 7 | 30 | |
| IIIA | 3 | 4 | | 5 | 21 | |
| IIIB | 0 | 1 | | 1 | 6 | |
| IV | 0 | 4 | | 2 | 5 | |
| Nodal Status (UICC) | | | | | | |
| N0 | 4 | 12 | 0.71† | 23 | 28 | 0.006† |
| N1 (1-6 positive) | 5 | 15 | | 9 | 52 | |
| N2 (7-15 positive) | 0 | 3 | | 4 | 16 | |
| N3 (≧16 positive) | 0 | 1 | | 2 | 3 | |
| Tumor Invasion | | | | | | |
| T1 | 2 | 2 | 0.68† | 15 | 24 | 0.02† |
| T2 | 4 | 19 | | 20 | 52 | |
| T3 | 3 | 10 | | 3 | 21 | |
| T4 | — | — | | 0 | 2 | |
| Curative Resection | | | | | | |
| Yes | 8 | 27 | 0.89 | — | — | — |
| No | 1 | 4 | | — | — | |

Meth: methylated COX-2 promoter; Unmeth: unmethylated COX-2 promoter. Correlations by Fisher's exact test;
*Calculated by Student T-test;
†Calculated by Mann-Whitney's U test

TABLE 2

Multivariate analysis of prognostic factors as co-variables with COX-2 methylation status for gastric cancer disease outcome*

| | Time to recurrence | | Overall survival | |
|---|---|---|---|---|
| | HR (95% CI) | P-value | HR (95% CI) | P-value |
| FAMTX trial | | | | |
| T-stage | — | 0.73 | — | 0.59 |
| Number of involved nodes | | | | |
| N0 (0) | 1 | 0.01 | 1 | 0.04 |
| N1 (1-6) | 3.70 (1.15-11.96) | 0.03 | 3.66 (1.31-10.14) | 0.01 |
| N2 (7-15) | 5.28 (0.53-52.91) | 0.16 | 3.10 (0.58-16.62) | 0.19 |
| N3 (≧16) | 159.59 (6.61-3852.78) | 0.002 | 16.18 (1.42-184.90) | 0.03 |
| TNM-stage | — | 0.60 | — | 0.53 |
| Curative resection | n.a. | n.a. | — | 0.39 |
| Randomization (surgery alone) | 0.23 (0.08-0.73) | 0.01 | 0.30 (0.12-0.71) | 0.008 |
| Intestinal type (Lauren) | — | 0.18 | — | 0.09 |
| COX-2 methylated | 0.08 (0.01-0.65) | 0.02 | 0.37 (0.14-1.00) | 0.05 |

TABLE 2-continued

Multivariate analysis of prognostic factors as co-variables with COX-2 methylation status for gastric cancer disease outcome*

| | Time to recurrence | | Overall survival | |
|---|---|---|---|---|
| | HR (95% CI) | P-value | HR (95% CI) | P-value |
| D1D2 trial | | | | |
| T-stage | — | 0.16 | — | 0.31 |
| Number of involved nodes | | <0.0001 | | <0.0001 |
| N0 (0) | 1 | | 1 | |
| N1 (1-6) | 8.67 (3.36-22.37) | <0.0001 | 1.68 (1.08-2.67) | 0.03 |
| N2 (7-15) | 24.25 (8.66-67.87) | <0.0001 | 4.53 (2.45-8.38) | <0.0001 |
| N3 (≧16) | 68.91 (18.32-259.27) | <0.0001 | 11.54 (4.17-31.92) | <0.0001 |
| TNM-stage | — | 0.17 | — | 0.38 |
| Randomization (D1 resection) | — | 0.65 | — | 0.85 |
| Intestinal type (Lauren classification) | 0.57 (0.35-0.95) | 0.03 | 0.63 (0.42-0.93) | 0.02 |
| COX-2 methylated | 0.49 (0.24-0.99) | 0.05 | 0.62 (0.38-0.99) | 0.05 |

*Stepwise Cox regression model; HR: Hazard Ratio; CI: Confidence Interval; n.a.: not applicable

TABLE 3

Comparison of clinical characteristics between selected and non-selected cases from curatively resected patients of the D1D2 trial

| | Patients receiving resection with curative intent from D1D2 trial (n = 711) | | |
|---|---|---|---|
| | Non-selected patients n = 533 | Selected patients n = 178 | |
| Factor | Number of patients (percent) | | P-value |
| Sex | | | |
| Female | 230 (42) | 80 (48) | 0.68 |
| Male | 303 (58) | 98 (52) | |
| Age | | | |
| Median (±SE) | 63.28 (0.52) | 66.32 (0.76) | 0.002 |
| Randomization | | | |
| D1 resection | 283 (53) | 97 (54) | 0.75 |
| D2 resection | 250 (47) | 81 (46) | |
| T-stage | | | |
| T0 | 7 (1) | 0 (0) | 0.11 |
| T1 | 137 (26) | 46 (26) | |
| T2 | 236 (45) | 97 (54) | |
| T3 | 144 (26) | 32 (28) | |
| T4 | 9 (2) | 3 (2) | |
| N-stage | | | |
| N0 | 238 (45) | 71 (40) | 0.21 |
| N+ | 295 (55) | 107 (60) | |

What is claimed is:

1. A method for determining a prognosis for a human gastric cancer patient, comprising:
   obtaining a gastric tumor tissue sample from the patient;
   extracting a genomic DNA sample from the gastric tumor tissue sample;
   determining a methylation status of the genomic DNA for a predetermined number of base pairs around the COX-2 promoter; and
   determining the prognosis of the patient, wherein the prognosis predicts a probability of survival for the patient, and wherein the methylation status of hypermethylation in the COX-2 promoter region indicates a favorable prognosis.

2. The method of claim 1, wherein a status of hypomethylation in the COX-2 promoter region indicates a poor prognosis.

3. The method of claim 1, wherein said predetermined number of base-pairs around the COX-2 promoter is −14 bp/+110 bp from a transcription site of the COX-2 promoter.

4. A method for determining a course of treatment for a human gastric cancer patient, comprising:
   obtaining a gastric tumor tissue sample from the patient;
   analyzing the gastric tumor tissue sample to determine a methylation status in the COX-2 promoter region with a predetermined number of base-pairs around the promoter to determine a prognosis, wherein the prognosis predicts a probability of survival for the patient, and wherein the methylation status of hypermethylation in the COX-2 promoter region indicates a favorable prognosis; and
   prescribing a course of treatment for the patient based on the prognosis.

5. The method of claim 4, wherein a methylation status of hypomethylation is determined and the prognosis is poor, an adjuvant therapy is prescribed.

6. The method of claim 1, wherein the prognosis further predicts a probability of recurrence-free survival.

7. The method of claim 1, wherein the prognosis further predicts a probability of overall survival.

8. The method of claim 5, wherein the adjuvant therapy is a COX-2 inhibitor.

9. The method of claim 8, wherein the COX-2 inhibitor is aspirin or celecoxib.

* * * * *

SEQUENCE LISTING

<160> NUMBER OF SEQ ID NOS: 9

<210> SEQ ID NO 1
<211> LENGTH: 25
<212> TYPE: DNA
<213> ORGANISM: Artificial
<220> FEATURE:
<223> OTHER INFORMATION: Methylation specific COX-2 forward primer

<400> SEQUENCE: 1
tttcggttag cgattattgt tatac        25

<210> SEQ ID NO 2
<211> LENGTH: 30
<212> TYPE: DNA
<213> ORGANISM: Artificial
<220> FEATURE:
<223> OTHER INFORMATION: Methylation specific COX-2 reverse primer

<400> SEQUENCE: 2
cgaaaataaa ctttactatc taaaaacgtc                               30

<210> SEQ ID NO 3
<211> LENGTH: 27
<212> TYPE: DNA
<213> ORGANISM: Artificial
<220> FEATURE:
<223> OTHER INFORMATION: Non-methylated-specific COX-2 forward primer

<400> SEQUENCE: 3
tttggttagt gattaattgt tatatga                                  27

<210> SEQ ID NO 4
<211> LENGTH: 30
<212> TYPE: DNA
<213> ORGANISM: Artificial
<220> FEATURE:
<223> OTHER INFORMATION: Non-methylated-specific COX-2 reverse primer

<400> SEQUENCE: 4
caaaaataaa ctttactatc taaaaacatc                               30

<210> SEQ ID NO 5
<211> LENGTH: 20
<212> TYPE: DNA
<213> ORGANISM: Artificial
<220> FEATURE:
<223> OTHER INFORMATION: Forward primer for the COX-2 promoter region

<400> SEQUENCE: 5 taagggaga ggagggaaaa                                           20

<210> SEQ ID NO 6
<211> LENGTH: 26
<212> TYPE: DNA
<213> ORGANISM: Artificial
<220> FEATURE:
<223> OTHER INFORMATION: Reverse primer for the COX-2 promoter region
<220> FEATURE:
<221> NAME/KEY: misc_feature
<222> LOCATION: (18)..(18)
<223> OTHER INFORMATION: n = a or g

<400> SEQUENCE: 6
cacctatata actaaacncc aaaacc                                   26

<210> SEQ ID NO 7
<211> LENGTH: 19
<212> TYPE: DNA
<213> ORGANISM: Artificial
<220> FEATURE:
<223> OTHER INFORMATION: Forward primer for COX-2 mRNA

<400> SEQUENCE: 7
catttgaaga acttacagg                                           19

<210> SEQ ID NO 8
<211> LENGTH: 16

```
<212> TYPE: DNA
<213> ORGANISM: Artificial
<220> FEATURE:
<223> OTHER INFORMATION: Reverse primer for COX-2 mRNA

<400> SEQUENCE: 8
ccaaagatgg catctg                                                    16

<210> SEQ ID NO 9
<211> LENGTH: 24
<212> TYPE: DNA
<213> ORGANISM: Artificial
<220> FEATURE:
<223> OTHER INFORMATION: Fluorescent labeled probe for COX-2 mRNA

<400> SEQUENCE: 9
ctccacagca tcgatgtcac cata                                           24
```